United States Patent
İçsel et al.

(10) Patent No.: US 9,839,643 B2
(45) Date of Patent: Dec. 12, 2017

(54) PALLADIUM COMPLEX WITH HIGH ANTICANCER ACTIVITY

(71) Applicants: ULUDAG ÜNIVERSITESI TTO, Nilüfer/Bursa (TR); Ceyda İçsel, Bursa (TR); Engin Ulukaya, Bursa (TR); Veysel Turan Yilmaz, Bursa (TR)

(72) Inventors: Ceyda İçsel, Bursa (TR); Engin Ulukaya, Bursa (TR); Veysel Turan Yilmaz, Bursa (TR); Konstantinos Dimas, Larissa (GR)

(73) Assignees: ULUDAG ÜNIVERSITESI TTO, Bursa (TR); Ceyda İçsel, Bursa (TR); Engin Ulukaya, Bursa (TR); Veysel Turan Yilmaz, Bursa (TR); Konstantinos Dimas, Larissa (GR)

( * ) Notice: Subject to any disclaimer, the term of this patent is extended or adjusted under 35 U.S.C. 154(b) by 0 days.

(21) Appl. No.: 15/317,500

(22) PCT Filed: May 11, 2015

(86) PCT No.: PCT/TR2015/000196
§ 371 (c)(1),
(2) Date: Dec. 9, 2016

(87) PCT Pub. No.: WO2015/171095
PCT Pub. Date: Nov. 12, 2015

(65) Prior Publication Data
US 2017/0106000 A1    Apr. 20, 2017

(30) Foreign Application Priority Data
May 9, 2014 (TR) .............................. a 2014 05244

(51) Int. Cl.
*A61K 31/555*    (2006.01)
*A61K 31/515*    (2006.01)
*A61K 31/24*    (2006.01)
*C07F 15/00*    (2006.01)
*A61P 35/00*    (2006.01)

(52) U.S. Cl.
CPC ................................ *A61K 31/555* (2013.01)

(58) Field of Classification Search
CPC ..... C07F 15/00; A61K 31/555; A61K 31/515; A61K 31/24; A61P 35/00
USPC .......................................................... 544/225
See application file for complete search history.

(56) References Cited

PUBLICATIONS

International Search Report for corresponding International Application No. PCT/TR2015/000196.

*Primary Examiner* — Kahsay Habte
(74) *Attorney, Agent, or Firm* — Egbert Law Offices, PLLC

(57) ABSTRACT

A compound of the formula in which X is an anion selected front $F^-$, $Cl^-$, $Br^-$, $I^-$, $NO_3^-$, $CH_3COO^-$, $CN^-$, $SCN^-$, $NCO^-$ and $ClO_4$ groups. This formula is obtained by synthezing a $[Pd(bpma)Cl]X \cdot H_2O$ complex, adding barbiturate salt to the complex and obtaining crystals of the complex.

8 Claims, 4 Drawing Sheets

PALLADIUM COMPLEX WITH HIGH ANTICANCER ACTIVITY

FIELD OF THE INVENTION

This invention refers to a novel palladium (II) complex having antitumor activity.

More particularly, the invention relates to a palladium (II) complex, ([Pd(bpma)(barb)]X·H$_2$O), having antitumor activity, its synthesis method, molecular structure and especially possible use in the treatment of colon cancer.

BACKGROUND OF THE ART

Cancer is a class of diseases characterized by abnormal cell division and out-of-control cell growth. In the treatment of cancer, some drugs are used to inhibit the cell growth or to kill the cancer cells. Cisplatin, oxaliplatin, carboplatin and nedaplatin are some of the important clinically used platinum-based anticancer drugs (1). It is believed that these drugs inhibit the growth of the cells via interaction with DNA (2). Although these commercial drugs are used for the treatment of various types of cancer, they show side effects due to their high toxicity on the normal cells (3). Therefore, they have some deleterious side on human health.

In the last decade, the investigation of anticancer activities of palladium complexes substantially increased due to their chemical similarity to the platinum based compounds (4). In addition, in vitro and in vivo studies of palladium complexes have shown promising results and they were even also found to be cytotoxic on cancer stem cells (5). As a result, works related to highly cytotoxic new palladium complexes became important in this field.

Palladium (II) complexes of 5,5-diethylbarbiturate have received less attention and in the literature, only one synthesis and structure of a complex (cis-[PdCl(barb)(PPh$_3$)$_2$], (PPh$_3$=triphenylphosphine) is reported (6). However, the anticancer activity of this complex is not known. On the other hand, a palladium (II) complex with bis(2-pyridylmethyl)amine (bpma), {[Pd(bpma)Cl](sac)·2H$_2$O, where sac is the saccharinate anion}, showed a cytotoxic effect on A549 cells, similar to cisplatin (7).

One of the patents in the literature concerning this subject matter is the patent application numbered U.S. Pat. No. 7,935,728B1. However, when the content of the application is evaluated, it is seen that it has a very different molecular formula.

American patent application numbered U.S. Pat. No. 4,584,316 is related to palladium(II) complexes with anticancer feature. However a complex with Pd(II)A$_m$X$_n$ structure is mentioned in said application.

Another invention numbered TR2011 000198B, which belongs to some of the present inventors, titled "New palladium(II) complexes with anticancer activity in low dosages". In said application, use of the complexes with the formulae of [Pd(terpy)(sac)](sac) and [Pd(terpy)Cl](sac) in the cancer therapy as anticancer drugs were mentioned. However, structures of mentioned compounds are different from the compound which is subject matter of the invention and xenograft studies on NOD/SCID mice about mentioned compound, an inevitably critical stage in the development of a cancer drug, were not performed. In the present application, the results of the xenograft studies on NOD/SCID mice are presented.

In conclusion, the technique of the prior art mentioned above fails to provide solutions to the existing problems, thus necessitates an improvement in the concerned technical field.

THE AIM OF THE INVENTION

The present invention relates to the synthesis, structure and anticancer activity of a palladium(II) complex which meets the aforementioned requirements, eliminates all disadvantages and introduces some additional advantages.

The main goal of the invention is to cure cancer which is very common nowadays, using a palladium(II) complex with high anticancer activity.

The aim of the invention is to prepare a palladium(II) complex having high anticancer activity in vitro and in vivo.

Another aim of the invention is to obtain a complex with low toxicity and so, it can be used in high doses in therapies.

Another aim of the invention is to use of a complex in different formulations in cancer therapy thanks to the high solubility feature that the complex have in various solvents.

The aim of the invention is to synthesize a complex having anticancer activity especially on colon cancer cells.

In order to fulfill the above requirements, a palladium complex with high anticancer activity, ([Pd(bpma)(barb)]X·H$_2$O), was prepared.

The structural and characteristic aspects and all the advantages of the present invention will be more clearly understood by means of the following figures and the detailed description written with references to these figures; therefore, while making an evaluation, these figures and the detailed description should be taken into account.

DETAILED DESCRIPTION OF THE INVENTION

In this detailed description, the preferred embodiments of the synthesis and possible structure of the palladium complex with high anticancer activity are described for a better understanding of the invention without any limiting effect.

The present invention is related to the synthesis, structure and in vitro and in vivo cytotoxic activity of the novel palladium complex and shows its suitability in the treatment of the colon cancer as a drug.

Figure 1:
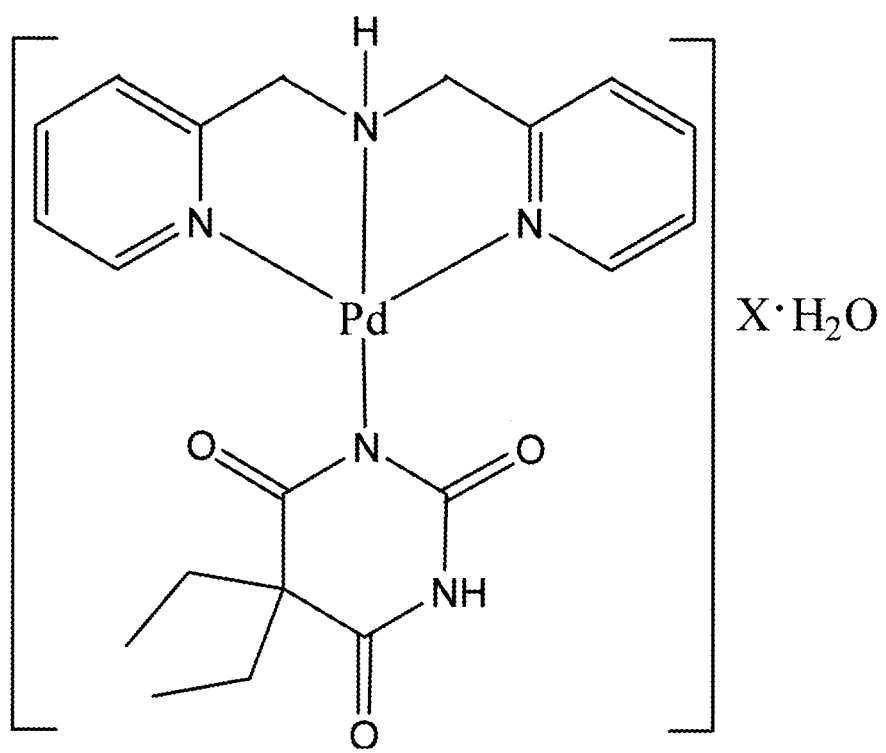
FIG. 1 presents the structure of [Pd(bpma)(barb)]X·H$_2$O complex.

The complex which is subject matter of the invention is described by a formula of [Pd(bpma)(barb)]X·H$_2$O. As shown in FIG. 1 and also below. The coordination sphere, in which the palladium(II) ion is coordinated by a tridentate bpma ligand and a monodentate barb anion, is stabilized by X ions, forming a solid salt.

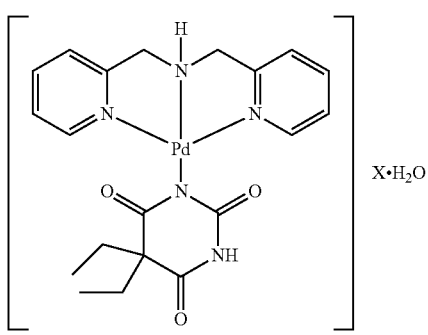

The structure of [Pd(bpma)(barb)]X·H$_2$O complex

X mentioned in complex corresponds to F$^-$, Cl$^-$, Br$^-$, I$^-$, NO$_3^-$, CH$_3$COO$^-$, CN$^-$, SCN$^-$, NCO$^-$ and ClO$_4^-$ anions. Bpma is the neutral bis(2-pyridylmethyl)amine molecule, while barb is the 5,5-diethylbarbiturate anion formed from the deprotonation of an NH hydrogen of 5,5-diethylbarbituric acid.

Synthesis and Characterization

The novel complex [Pd(bpma)(barb)]Cl·H$_2$O can be synthesized by two different methods:

Method 1:

The starting complex [Pd(bpma)Cl]Cl·H$_2$O was synthesized as described in the literature (8). 5 mL aqueous solution of Na(barb) (0.5 mmol, 0.11 g), which is chosen as a barbiturate salt, was added directly to a 15 mL aqueous solution of [Pd(bpma)Cl]Cl·H$_2$O (0.5 mmol). The resulting clear yellow solution was stirred until 60° C. for until 2 hour and allowed to stand at room temperature for crystallization. Yellow crystals of [Pd(bpma)(barb)]Cl·H$_2$O complex formed after three days. After that, obtained crystals dried in open air.

Method 2:

[Pd(bpma)Cl]Cl·H$_2$O (0.5 mmol) and solid AgNO$_3$ (1 mmol, 0.17 g) which is chosen as a water soluble silver salt in water were stirred together in 200 mL of water and set to reflux until 6 hour. The precipitate of AgCl$_{(s)}$ in the solution which is obtained after reflux cooled to room temperature was removed by filtering through Celite paste. The clear solution volume in solution phase was evaporated to 25 mL in evaporator. The mixture obtained after Na(barb) (1 mmol, 0.21 g) were added to the evaporated solution is stirred at 60° C. for half an hour and then the precipitate cooled to a room temperature and filtered off. Yellow colored [Pd(bpma)(barb)]Cl·H$_2$O crystals formed from the solution were obtained and dried in open air.

The structure of the crystals were identified by elemental analysis (Costech), FT-IR (Thermo Nicolet 6700) and single crystal X-ray diffraction (STOE IPDS-II).

The solubility of [Pd(bpma)(barb)]ClH$_2$O: It dissolves in water, pure DMSO, pure DMF and also the mixtures of ethanol-water or acetonitrile-water. The solubility of the complex in common solvents makes it suitable to prepare various formulations. In addition, it is also possible for parenteral (subcutaneous, intravenous) applications.

Elemental analysis of [Pd(bpma)(barb)]Cl·H$_2$O complex: C$_{20}$H$_{26}$ClN$_5$O$_4$Pd; MW, 542.31. Mp. (° C.): 220-235 (decomposition). Analysis results % C 44.3 (44.6); H 4.8 (4.7); N 12.7 (13.0); calculation values % C 44,6; % H 4,7; % N 13,0.

FT-IR spectral data of [Pd(bpma)(barb)]Cl·H$_2$O complex: ν (cm$^{-1}$): ν(OH) 3494 m, 3348 m, ν(NH) 3277 w, 3176 b, ν(CH) 3130 wv-2778 w, ν(C=O) 1727 m, 1675 s, ν(C=N) 1618 vs, ν(C=C) 1477 w, 1440 m (b: broad, s: strong, vs: very strong, w: weak, vw: very weak, m: medium).

Single crystal X-ray diffraction data of [Pd(bpma)(barb)]Cl·H$_2$O complex: T=296 K, triclinic (P$\bar{1}$), a=7.7720(4) Å, b=8.5649(5) Å, c=17.2424(10) Å, α=101.450(4)°, β=95.927(5)°, γ=93.653(5)°, V=1114.73(11) Å$^3$, Z=2, D$_x$=1.616 g cm$^{-3}$, R$_1$[I>2σ]=0.0354, wR$_2$=0.0837, S=1.045.

In the IR spectrum of the palladium complex, the band at 3500 cm$^{-1}$ corresponds to the water of crystallization. The NH group of the barb ligand appears at 3176 cm$^{-1}$ as a weak band, while the carbonyl groups occur at 1727 and 1675 cm$^{-1}$ as medium and strong bands. The bpma ligand is characterized by its NH band at 3277 cm$^{-1}$.

Single crystal X-ray measurements shows that, in subject matter complex; palladium forms a coordinate covalent bond with three N atoms of bpma ligand and deprotonated N atom of barb ligand. The resulting complex cation interacts with the chloride anion. The crystal water molecules further reinforce the interactions between the ions via hydrogen bonds.

Figure 2:
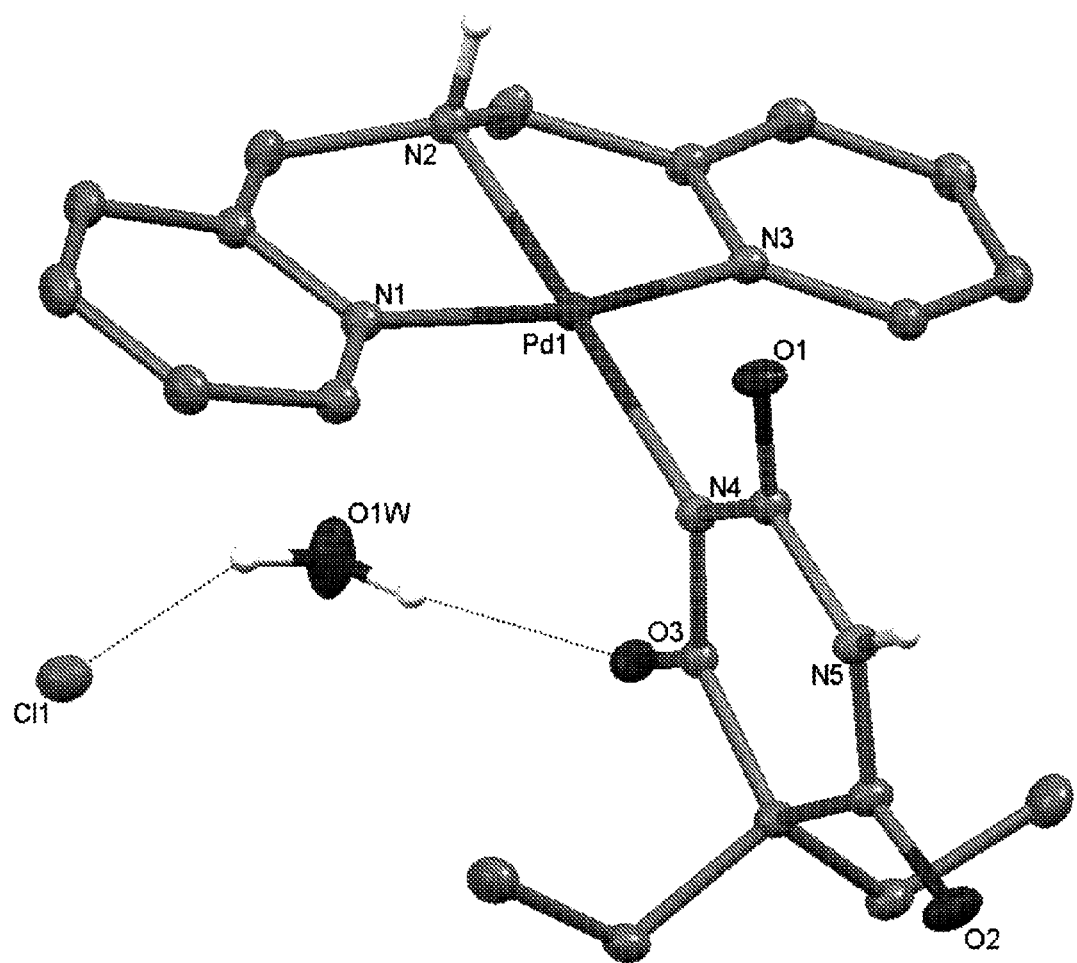
FIG. 2 presents the molecular structure of [Pd(bpma)(barb)]Cl·H$_2$O complex determined by X-ray diffraction technic.

The X-ray structure of the complex is shown in FIG. 2. The bond distances found in the complex: Pd1N1 =2.014(3) A, Pd1N2 =2.003(3) A, Pd1N3 =2.024(2) A, Pd1N4 =2.058(2) A.

Tests for Anticancer Activity

In vitro Tests

Cell Lines:

Anticancer activity tests were made on colon (HCT116, HT29, HCT15), lung (A549, H460) and ovarian (OVCARS, OVCAR3, NCI-ADRRES) cancer cell lines in vitro. All cell lines were obtained from American Type Culture Collection (Manassas, Va., USA) or American National Cancer Institute (NCI, USA). All cell lines were grown in RPMI1640 medium supplemented with 25 mM HEPES, 2 mM L-Glutamine, 5-10% fetal calf serum and antibiotics at 37° C. in a humidified 5% CO$_2$ atmosphere.

SRB Assay:

The effect of the aforementioned compound on the selected cell lines indicated above was tested with Sulforhodamine B (SRB) assay that is also used by American National Cancer Institute. 100 μL of cancer cells were seeded at densities between 5.000-40.000 per well of a 96 well plate. The cells were incubated for 24 h for adaptation. Then, the tested complex and anticancer drugs (cisplatin, oxaliplatin and carboplatin) were added. The tested complex was dissolved in DMSO at 100 μM initial concentration and diluted to obtain 10 different concentrations as 1:2, 1:4 or 1:10. Every different concentration was analyzed in triplicates and in two independent experiments. The cells were fixed with 50% (w/v) ice-cold TCA in situ after 48 hour incubation. SRB dye bound to the cells was dissolved by unbuffered 10 mM Tris solution and absorbance values were measured at 530 nm in an ELISA microplate reader. Percentages for cell growth that were calculated from absorbance measurements (initial: T$_z$, control: C, complex at different concentrations: T$_i$) are as described below:

GI$_{50}$ (dose inhibiting 50% cell growth)=[T$_i$−T$_z$)/(C−T$_z$)]×100=50

TGI (total growth inhibition): T$_i$=T$_z$

LC$_{50}$ (dose killing 50% of initially seeded cells)=[(T$_i$−T$_z$)/T$_z$]×100=−50

Cytotoxic effects of the subject of the invention, palladium(II) complex, and clinically used anticancer drugs, cisplatin, oxaliplatin and carboplatin on selected cell lines were given in Table 1. Novel palladium(II) complex is selectively effective on HCT116, HT29 and HCT15 colon cancer cell lines compared to anticancer drugs.

TABLE 1

Cytotoxic activities of [Pd(bpma)(barb)]Cl•H$_2$O and clinically used anticancer drugs on studied cell lines.

| | HCT116 | HT29 | HCT15 | A549 | H460 | OVCAR5 | OVCAR3 | NCI-ADRRES |
|---|---|---|---|---|---|---|---|---|
| [Pd(bpma)(barb)]Cl•H$_2$O | | | | | | | | |
| GI$_{50}$ | 4.9 | 3.0 | 6.8 | 43.1 | 44.4 | 40.0 | 6.5 | 5.6 |
| TGI | 9.1 | 6.6 | 9.9 | 80.1 | 75.9 | 63.5 | 25.2 | 10.0 |
| LC$_{50}$ | 82.4 | 22.0 | 89.1 | >100 | >100 | 87.0 | >100 | >100 |
| Cisplatin | | | | | | | | |
| GI$_{50}$ | 24.8 | 29.8 | 57.3 | 6.6 | 8.9 | 57.8 | 34.3 | 9.9 |
| TGI | 90.2 | 92.0 | 85.9 | 55.1 | 50.3 | >100 | >100 | >100 |
| LC$_{50}$ | >100 | >100 | >100 | >100 | 95.9 | >100 | >100 | >100 |
| Oxaliplatin | | | | | | | | |
| GI$_{50}$ | 0.9 | 6.3 | 6.0 | 4.4 | 6.8 | 50.7 | 9.1 | 24.8 |
| TGI | 64.1 | 56.5 | 17.2 | 58.2 | 95.6 | >100 | >100 | >100 |
| LC$_{50}$ | >100 | >100 | >100 | >100 | >100 | >100 | >100 | >100 |
| Carboplatin | | | | | | | | |
| GI$_{50}$ | >100 | >100 | >100 | >100 | >100 | >100 | >100 | >100 |
| TGI | >100 | >100 | >100 | >100 | >100 | >100 | >100 | >100 |
| LC$_{50}$ | >100 | >100 | >100 | >100 | >100 | >100 | >100 | >100 |

In vivo Tests:

Xenograft studies were made by using HCT116 colon cancer cell lines after observing that the subject of the invention, palladium(II) complex, is especially effective on colon cancer cells. The results are compared to oxaliplatin effect which is used clinically for the treatment of colon cancer. To obtain the xenografts, approximately 10$^6$ cells from exponentially growing HCT116 cells were intradermally injected in the axillae of 6-8 weeks old NOD/SCID mice by using the English double sided trocar implantation method. Two separate injections were made to each mouse. Two tumor inocula were added to each mouse in order to produce one tumor load for each mouse. Hence, the total mouse number was lowered and differences arising from mouse to mouse were decreased. These positive effects are the beneficial aspects of the English system.

Treatment was started in randomly chosen animal groups when the tumor volume reached 100-200 mm$^3$. Applied doses were selected as 40 mg/kg for the novel palladium(II) complex and 5 mg/kg for oxaliplatin. The treatment was performed in 5 days of application and 2 days of resting periods. Tumor volume was calculated from [(axb$^2$)/2] formula. In this formula, a and b are tumor length and width which are measured by vernier caliper. Measurements were repeated twice weekly. Treated animals received a single dose from the drugs. Apart from tumor volume, ΔT/ΔC % values were calculated from ΔT=T−D$_0$ and ΔC=C−D$_0$ equations. D$_0$ is the mean tumor volume at the beginning of the treatment, T is the mean tumor volume of treated mice and C is the mean tumor volume of untreated (not injected with complex) mice which is used as a control. Optimum ΔT/ΔC % value was used as a measure of drug activity and highly active compounds have values less than 42%. Weight loss, neurological disorders and changes in diet were recorded as indication of toxicity (side effects). The experiments were terminated when the tumor volume reached approximately to 1000-1500 mm$^3$.

Figure 3:
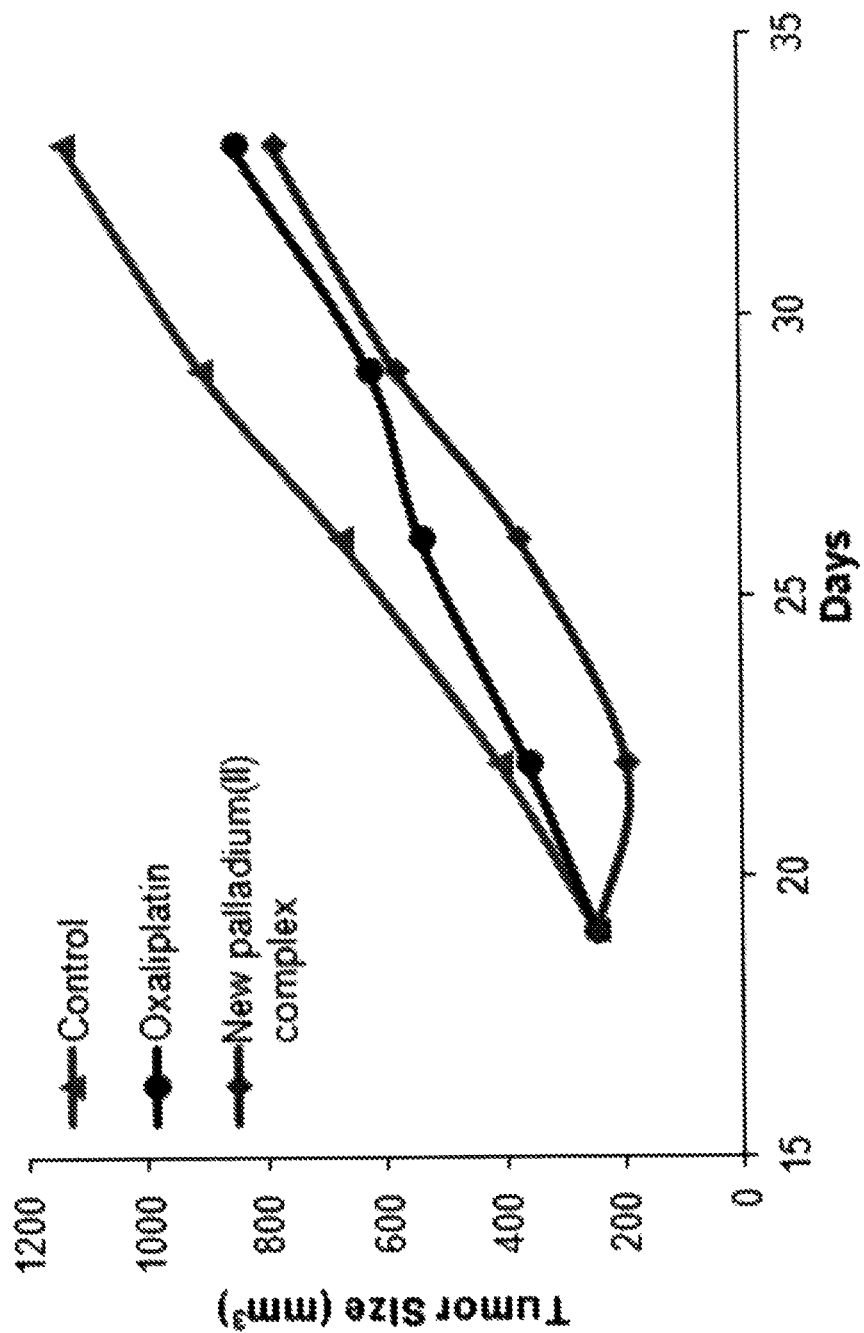
FIG. 3 presents the effects of [Pd(bpma)(barb)]Cl·H$_2$O and oxaliplatin on the tumor size in mice transplanted with HCT116 cancer cells.
Figure 4:
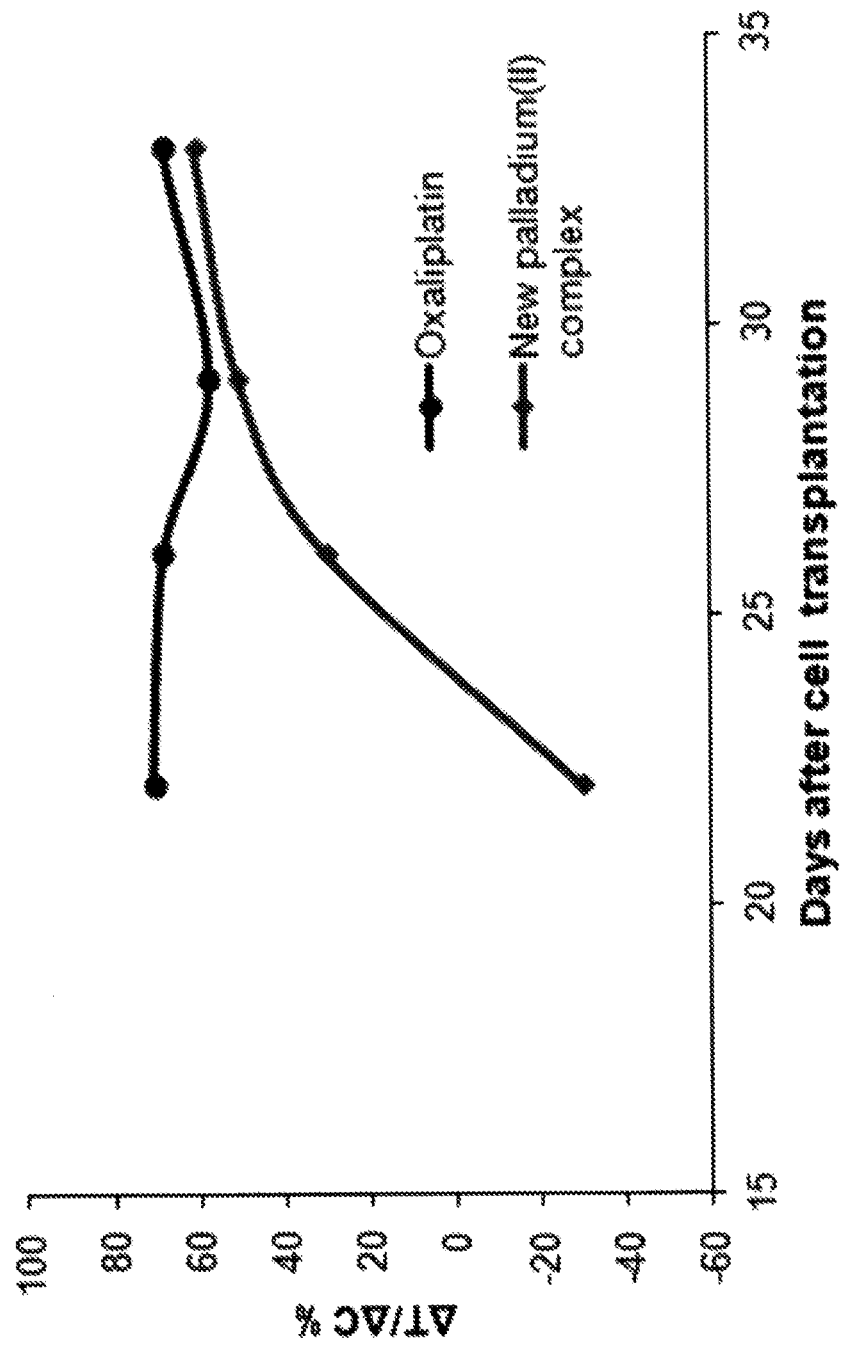
FIG. 4 presents the ΔT/ΔC % values of [Pd(bpma)(barb)]Cl·H$_2$O and oxaliplatin on the tumor size in mice transplanted with HCT116 cancer cells.

The results obtained from in vivo studies are given in Table 2 and FIG. 3-4. It is clear that the subject of the invention decreased the tumor volume more effectively than oxaliplatin in all time points of measurement. ΔT/ΔC % value was found as −29.88% for the complex where it was found as +70.60% for oxaliplatin on day 22. This effect shows that the acute cytotoxic effect of the complex is very powerful. From this point of view, the complex is multiple times more cytotoxic than oxaliplatin. There was no obvious difference in chronic effects, although the effect of the complex is higher. Chronic effect might be strengthened by increased doses or more frequent treatments.

TABLE 2

The effects of [Pd(bpma)(barb)]Cl•H$_2$O and oxaliplatin on the tumor size in mice transplanted with HCT116 cancer cells.

| Day | Control (Untreated) | [Pd(bpma)(barb)]Cl•H$_2$O | Oxaliplatin |
|---|---|---|---|
| 19 | 245.96 | 245.96 | 245.96 |
| 22 | 409.92 ± 92.88 | 195.61 ± 151.45 | 361.82 ± 153.96 |
| 26 | 675.16 ± 191.99 | 373.88 ± 157.42 | 538.00 ± 203.51 |
| 29 | 906.16 ± 282.88 | 577.38 ± 157.37 | 622.29 ± 152.76 |
| 33 | 1135.04 ± 285.03 | 782.22 ± 228.55 | 847.06 ± 176.45 |

REFERENCES

1. Calved, A. H., Harland, S. J., Newell, D. R., Siddik, Z. H., Jones, A. C., McElwain, T. J., Raju, S., Wiltshaw, E., Smith, I. E., Baker, J. M., Peckham, M. J., Harrap, K. R., Cancer Chemotherapy and Pharmacology, 9: 140-147, (1982); Hambley T. W., Coord. Chem. Rev., 166: 181-223, (1997); Graham J., Mushin M., Kirkpatrick P., Nature Reviews Drug Discovery 3: 11-12 (2004); Alderden R. A., Hall M. D., Hambley T. W., J. Chem. Ed. 83: 728-734 (2006)
2. Rosenberg B., VanCamp L., Trosko J. E., Mansour V. H., Nature 222: 385-386 (1969); Cleare M. J, Hoeschele J. D., Bioinorg. Chem. 2: 187-210 (1973); Lippard S. J., Science 218: 1075-1082 (1982); Jordana P., Carmo-Fonseca M., Cell. Mol. Life Sci. 57: 1229-1235 (2000)
3. Ebert, U., Loffler, H., Kirch, W., Pharmacology & Therapeutics, 74: 207-220 (1997); Spencer C. M., Goa K. L., Drugs, 50: 1001-1031 (1995)
4. Caires A. C. F., Anti-Cancer Agents in Medicinal Chemistry, 7: 484-494, (2007); Garoufis A., Hadjikakou S. K., Hadjiiliadis N., Coord. Chem. Rev., 253: 1384-1397 (2009)

5. Ulukaya E., Ari F., Dimas K, Ikitimur E. I., Guney E., Yilmaz V. T., Eur. J. Med. Chem. 46: 4957-63 (2011); Ulukaya E., Frame F., Cevatemre B., Pellacani D., Walker H., Mann V. M., Simms M. S., Stower Yilmaz V. T., Maitland N. J., PLoS One, 8: e64278 (2013)
6. Hague N., Coordination Chemistry of Barbituric Acid, Its Diethyl Derivative and
Benzildiimine with Transition Metals, (Ph.D. Thesis), Ludwig-Maximilians-Universitat
7. München, Germany, (2009)
8. Guney E., Yilmaz V.T., Ari F., Buyukgungor O., Ulukaya E., Polyhedron, 30: 114-122 (2011)
9. Pitteri, B., Annibale, G., Marangoni, G., Bertolasi, V., Ferretti, V., Polyhedron, 21: 2283-2291 (2002)

The invention claimed is:
1. A compound shown in formula (I):

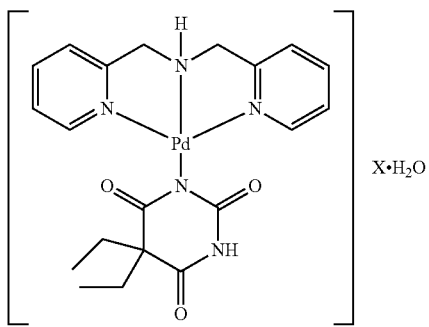

(I)

and the letter X is an anion selected front $F^-$, $Cl^-$, $Br^-$, $I^-$, $NO_3^-$, $CH_3COO^-$, $CN^-$, $SCN^-$, $NCO^-$ and $ClO_4^-$ groups, in which an oxidation number of Pd is (II) and the whole complex is +1.

2. A method for obtaining the formula (I) of claim 1 comprising:
   synthesizing a [Pd(bpma)Cl]X.H$_2$O complex;
   obtaining a solution after addition of barbiturate salt to the [Pd(bpma)Cl]X.H$_2$O complex; and
   obtaining [Pd(bpma)(barb)]X.H$_2$O crystals.

3. The method of claim 2, wherein before the addition of barbiturate salt to the [Pd(bpma)Cl]X.H$_2$O complex the steps of:
   obtaining a solution with a reflux of water soluble silver salt in water after addition to the synthesized [Pd(bpma)Cl]X.H$_2$O complex;
   removing AgCl$_{(s)}$ precipitate from the solution; and
   evaporating a remaining solution after the removal AgCl$_{(s)}$ precipitate.

4. The method of claim 2, wherein the method is performed up to 60° C. temperature and for 2 hours.

5. The method of claim 2, wherein said barbiturate salt is Na(barb).

6. The method of claim 2, wherein said water soluble silver salt is AgNO$_3$.

7. A method of treating a patient suffering from colon cancer comprising administering the compound of claim 1.

8. The method of claim 7, wherein said compound is applied parenterally.

* * * * *